US010267725B2

(12) United States Patent
Keightley et al.

(10) Patent No.: US 10,267,725 B2
(45) Date of Patent: Apr. 23, 2019

(54) SURFACE PROFILE MEASUREMENT SYSTEM

(71) Applicant: 3DM Devices Inc., Aldergrove (CA)

(72) Inventors: John Howard Keightley, Abbotsford (CA); Adriano Goncalves Cunha, Surrey (CA)

(73) Assignee: Evolution Engineering Inc., Calgary (CA)

( * ) Notice: Subject to any disclaimer, the term of this patent is extended or adjusted under 35 U.S.C. 154(b) by 0 days.

(21) Appl. No.: 15/987,025

(22) Filed: May 23, 2018

(65) Prior Publication Data

US 2018/0348116 A1   Dec. 6, 2018

Related U.S. Application Data

(60) Provisional application No. 62/514,607, filed on Jun. 2, 2017.

(51) Int. Cl.
| G01N 21/03 | (2006.01) |
| E21B 47/00 | (2012.01) |
| G02B 23/02 | (2006.01) |
| G02B 23/24 | (2006.01) |
| G01N 21/954 | (2006.01) |

(52) U.S. Cl.
CPC ..... *G01N 21/0332* (2013.01); *E21B 47/0002* (2013.01); *G01N 21/954* (2013.01); *G02B 23/02* (2013.01); *G02B 23/2484* (2013.01)

(58) Field of Classification Search
CPC .............. G01N 21/0332; G01N 21/954; E21B 47/0002; G02B 23/02

USPC .............................................. 356/606, 241.1
See application file for complete search history.

(56) References Cited

U.S. PATENT DOCUMENTS

| 4,839,526 | A | * | 6/1989 | Pryor | ................... | G01B 11/007 |
| | | | | | | 250/559.29 |
| 4,983,043 | A | | 1/1991 | Harding | | |
| 5,615,003 | A | | 3/1997 | Hermary et al. | | |
| 5,663,758 | A | | 9/1997 | Linville | | |
| 6,078,867 | A | | 6/2000 | Plumb et al. | | |
| 6,580,449 | B1 | | 6/2003 | Meltzer | | |
| 7,529,577 | B2 | * | 5/2009 | Jensen | ................... | A61B 1/227 |
| | | | | | | 356/241.1 |
| 7,751,038 | B2 | | 7/2010 | Vessereau et al. | | |
| 7,884,951 | B2 | | 2/2011 | Prouvost et al. | | |

(Continued)

FOREIGN PATENT DOCUMENTS

| DE | 102014215931 A1 | 3/2016 |
| WO | 2007029038 A1 | 3/2007 |

(Continued)

*Primary Examiner* — Roy M Punnoose
(74) *Attorney, Agent, or Firm* — Oyen Wiggs Green & Mutala LLP

(57) ABSTRACT

Apparatus for measuring surface profiles within passages such as the interiors of pipes, tubing, casing or the like includes an optical scanning system that acquires digital data that directly identifies the surface profiles. A temperature control system facilitates operation in high temperature environments. The optical scanning system may include a camera located between a light source and a conical mirror. Light deflecting elements may guide light from the light source to the conical mirror along a path that reverses direction.

21 Claims, 10 Drawing Sheets

(56) References Cited

U.S. PATENT DOCUMENTS

| | | | |
|---|---|---|---|
| 8,035,823 B2 * | 10/2011 | Keightley | G01B 11/2513 |
| | | | 356/606 |
| 8,528,668 B2 | 9/2013 | Rasheed | |
| 8,841,603 B1 | 9/2014 | Blanton et al. | |
| 8,842,273 B2 | 9/2014 | Bergman et al. | |
| 8,925,213 B2 | 1/2015 | Sallwasser | |
| 9,062,531 B2 | 6/2015 | Jones | |
| 9,080,429 B2 | 7/2015 | Hallundbaek et al. | |
| 2004/0114793 A1 * | 6/2004 | Bondurant | G01N 21/954 |
| | | | 382/141 |
| 2004/0136010 A1 * | 7/2004 | Jensen | A61B 1/227 |
| | | | 356/601 |
| 2010/0060904 A1 * | 3/2010 | Keightley | G01B 11/2513 |
| | | | 356/608 |
| 2012/0211649 A1 * | 8/2012 | Hallundbæk | E21B 47/102 |
| | | | 250/267 |
| 2013/0011102 A1 | 1/2013 | Rinzler et al. | |
| 2013/0319984 A1 | 12/2013 | Linyaev et al. | |
| 2015/0177409 A1 | 6/2015 | Sofiienko et al. | |
| 2016/0084008 A1 | 3/2016 | Faircloth et al. | |
| 2016/0187528 A1 | 6/2016 | Sofiienko et al. | |
| 2016/0202390 A1 | 7/2016 | Ramsay et al. | |
| 2016/0327775 A1 * | 11/2016 | Esteban Finck | G01B 11/24 |
| 2018/0156738 A1 * | 6/2018 | Wagner | G01B 11/306 |

FOREIGN PATENT DOCUMENTS

| | | |
|---|---|---|
| WO | 2011115601 A1 | 9/2011 |
| WO | 2016007642 A1 | 1/2016 |

\* cited by examiner

SURFACE PROFILE MEASUREMENT SYSTEM

CROSS-REFERENCE TO RELATED APPLICATION

This application claims the benefit under 35 U.S.C. § 119 of U.S. Application No. 62/514,607 filed 2 Jun. 2017 and entitled SURFACE PROFILE MEASUREMENT SYSTEM which is hereby incorporated herein by reference for all purposes.

FIELD

This invention relates to apparatus and methods for optically measuring the profiles of surfaces. A non-limiting example application of the invention is inspecting surfaces inside pipes and tubes.

BACKGROUND

Accurate measurements of surface profiles are useful in a wide range of applications. An example application is measuring surface profiles inside the bores of casing or production tubing in wellbores (e.g. oil and gas wells). Surface profile measurements can help to identify problems such as corrosion, wear and the like.

Some surface profilers operate using optical triangulation. Examples of surface profilers that operate using the principle of optical triangulation are described in commonly owned US patent Keightley et al. 8035823 issued on 11 Oct. 2011, which is hereby incorporated herein by reference for all purposes as if fully set out herein.

Apparatus for some downhole applications must be capable of operating in harsh environmental conditions of pressure and/or temperature. Pressures in some wellbores can be hundreds or thousands of pounds per square inch. Temperatures in some wellbores can exceed 150° C.

References describing apparatus for surface profiling include:
U.S. Pat. No. 4,983,043;
U.S. Pat. No. 5,615,003;
U.S. Pat. No. 5,663,758;
U.S. Pat. No. 6,580,449;
U.S. Pat. No. 7,751,038;
U.S. Pat. No. 7,884,951;
U.S. Pat. No. 8,528,668;
U.S. Pat. No. 8,841,603;
U.S. Pat. No. 8,842,273;
U.S. Pat. No. 8,925,213;
U.S. Pat. No. 9,062,531;

There remains a need for improved systems and methods for making surface profile measurements.

SUMMARY

This invention has a number of aspects. These aspects may be practiced in combination but also have application individually or in sub-combinations. These aspects include, without limitation:
- autonomous surface profile measuring apparatus suitable for use in downhole applications;
- temperature-controlled surface profile measurement apparatus and related methods;
- optical surface profile measurement apparatus having a novel optical arrangement and related methods;
- methods and apparatus for autonomous measurement of surface profiles simultaneously with one or more of downhole pressure, temperature, and borehole trajectory;
- methods and apparatus for autonomous measurement using video recording and surface playback;
- methods and apparatus for processing and displaying surface profile information.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
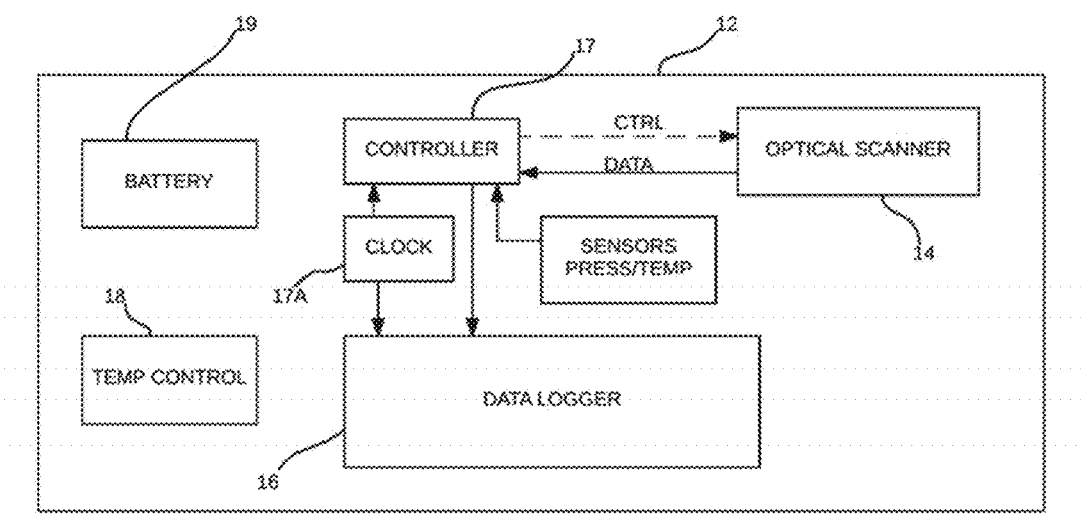
FIG. 1 is a block diagram that schematically depicts a surface profile measurement apparatus according to an example embodiment of the invention.

FIG. 1 shows schematically a surface profile measurement apparatus 10 according to an example embodiment of the invention. Apparatus 10 includes certain features that are advantageous for use in downhole environments. However, apparatus 10 may also be used in other applications.

Apparatus 10 comprises a body 12 that contains an optical scanning system 14, a data logging system 16, a controller 17 and a temperature control system 18. In the illustrated embodiment controller 17 comprises a real-time clock 17A. Apparatus 10 is self-contained and includes a battery power supply 19 which powers optical scanning system 14, data logging system 16 and controller 17.

Figure 1A:
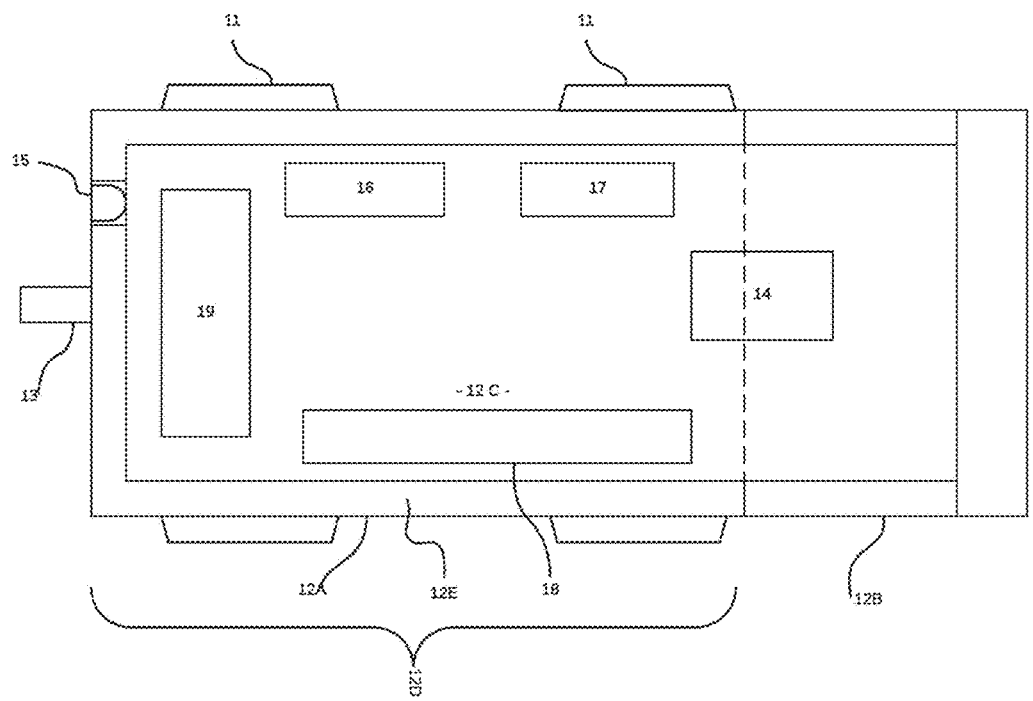
FIGS. 1A and 1B illustrate apparatus according to example embodiments.

As shown in FIG. 1A, body 12 may comprise a housing 12A designed to resist pressures expected when apparatus 10 is deployed. The illustrated housing 12A comprises a window 12B. Window 12B extends around housing 12 to provide a clear field of view in every direction for optical scanner 14. Window 12B may, for example, comprise a tube of a material that is substantially transparent to light used by optical scanning system 12.

In the illustrated embodiment, body 12 comprises a fitting 13 for coupling apparatus 10 to a wireline or slickline. One or more electrical ports 15 may be provided on the exterior of housing 12 and/or accessible by opening housing 12. Port(s) 15 may be electrically connected for functions such as configuring the operation of apparatus 10 (e.g. by programming controller 17), charging batteries 19 and downloading data from data logger 16. In some embodiments, port(s) 15 include a standard data communication port such as an Ethernet port, a USB port or the like. In addition to or instead of ports 15, apparatus 10 may include one or more wireless data transceivers (e.g. a WiFi, or Bluetooth™ data transceiver) by way of which data and/or instructions may be sent to and/or received from apparatus 10.

Apparatus 10 is dimensioned to be received in the bore of a tube, pipe conduit, passage, or the like to be scanned by optical scanning system 14. By way of non-limiting example, apparatus 12 may be dimensioned to fit into production tubing having an inside bore diameter of 1.9 inches. For example, a housing of apparatus 10 designed for use with such production tubing could have an outside diameter of 1.75 inches.

Apparatus 10 may include features that help to centralize apparatus 10 within a passage being studied such as a cylindrical bore of a casing, pipe, tube or the like. Centralizing apparatus 10 can help to keep windows of apparatus clean by reducing or avoiding contact with contaminants that may be on a wall of the bore. Centralizing apparatus 10 may also help to prevent apparatus 10 from impacting a wall of the bore with sufficient force to damage apparatus 10. In the illustrated implementations, optical scanning system 14 may provide a complete 360 degree profile of a bore wall relative to a reference origin defined by optical scanning system 14. In such embodiments, centralization of apparatus 10 is not required for obtaining accurate surface profile measurements.

Centralizing features may comprise, for example, resilient bows or arms and/or a surface of apparatus 10 that extends radially outwardly to provide a reasonably close but sliding fit into a passage being studied. For example, apparatus 10 may be dimensioned to fit into a pipe, tube, casing or the like with a clearance of 1/16 inch (about 1.6 mm) on all sides.

In the illustrated embodiment, apparatus 10 comprises wipers 11 that act to centralize apparatus 10 in a bore and also to keep window 12B from contacting a surface of the bore. Wipers 11 may be made of a slippery material such as Teflon™, for example. Wipers 11 may be field replaceable with wipers that extend radially by different distances for use in bores of different diameters.

At least some electronics of apparatus 10 are contained in a thermally-protected volume 12C within a thermally-insulating part of housing 12A. In the illustrated embodiment, housing 12A includes a double-walled part 12D that substantially encloses volume 12C. A space 12E between inner and outer walls of double-walled part 12D is evacuated to provide a vacuum flask that encloses temperature control system 18 and certain electronics of apparatus 10 that are located in thermally-protected volume 12C. Additional thermal insulation, for example, in the form of one or more of heat mirror films and materials having low thermal conductivity may optionally be provided to slow the rate at which heat can enter volume 12C.

In some embodiments, the thermal insulation of volume 12C is such that when apparatus 10, initially at room temperature (20° C.), is placed into an environment having a temperature of 150° C., temperature control system 18 can maintain the temperature within volume 12C below 60° C. for at least 2 hours. A prototype system has been successfully tested for 1.6 hours in an ambient temperature of 120° C.

In an example application, apparatus 10 is turned on and lowered into a wellbore through a casing or production tubing on a slickline. As apparatus 10 progresses along the wellbore, optical scanning system 14 measures a surface profile of the inside of the casing or production tubing.

Optical scanning system 14 may record the surface profile at a large number of points. For example, apparatus 10 may operate optical scanning system 14 to measure surface profile at each of 32 or more points spaced circumferentially about an inside surface of a tubular such as a casing or production tubing through which apparatus 10 is being lowered. In some embodiments, the points are equally angularly spaced apart relative to an axis of apparatus 10. The axis may, for example, coincide with a longitudinal centerline of apparatus 10. The number of points may be selected to obtain a surface profile measurement having a desired resolution in the circumferential direction. For example, if a casing has an inside diameter of 10 cm and apparatus 10 obtains measurements at 256 points angularly spaced apart around apparatus 10 then the measured points will be spaced apart by about 1.2 mm in the circumferential direction.

In some embodiments, apparatus 10 is configured to scan a bore with a resolution of at least about ¼ inch (about 6.5 mm) in both circumferential and longitudinal directions. Such scanning may yield a point cloud that records the profile of the surface surrounding apparatus 10. This point cloud may be processed to identify areas of interest (e.g. areas where the surface may be worn, corroded or otherwise compromised).

The resolution of the point cloud may be different in circumferential and axial directions. It is typically convenient to provide a circumferential resolution that is significantly higher than the axial resolution. For example, optical scanning system 14 may be configured to measure positions of 200, 250, 400, 500 or more points spaced apart around the circumference of a bore in which apparatus 10 is located. For example, for bores having diameters of 10 inches (25.4 centimeters) or less an apparatus 10 centered in the bore and configured to acquire 400 points equally angularly spaced apart will acquire points with a distance between adjacent circumferential points of about 0.08 inches or less. In some embodiments, optical scanning system 14 acquires points with an angular separation between adjacent points of 1 degree or less.

Apparatus 10 may repeat this measurement at locations spaced longitudinally apart along the tubing. The resulting data may be stored in data logging system 16. The data stored in data logging system 16 may comprise raw data from which surface profile information can be calculated or surface profile information calculated by controller 17.

In some embodiments, apparatus 10 is configured to periodically measure the profile on the surface of a set of points on a circumference of the surface at one longitudinal position along the surface. The longitudinal spacing of sets of measured points is then determined by intervals between measurements and the speed at which apparatus 10 is being moved along the wellbore. For example, if apparatus 10 is being lowered or raised in a wellbore at a rate of 25 cm/sec and a measurement of one set of points is taken every 1/50 second then the resolution of the surface profiling in the longitudinal direction will be about 5 mm.

Apparatus 10 may include a real-time clock (e.g. clock 17A). The time that each set of measured points is acquired may be logged by data logging system 16. If apparatus 10 is at a known position at an initial time and apparatus 10 is subsequently moved along the wellbore with a known velocity profile—conveniently a constant velocity —then the position of apparatus 10 at times when sets of points are measured may be inferred.

In some embodiments, a winch being used to position apparatus 10 in a wellbore is equipped with an encoder, a real-time clock and a data logger that is configured to log position of apparatus 10 in the wellbore as a function of time. After apparatus 10 has been recovered, data from data logging system 16 may be combined with data from the data logger associated with the winch to associate a position in the wellbore with each set of measured points.

The speed of travel of apparatus 10 may be selected based on the rate at which apparatus 10 can measure points and log the resulting data. In some embodiments, apparatus 10 is moved along a bore at a rate of approximately 100 feet/minute (about 50 cm/sec). In some embodiments, apparatus 10 is moved along a bore at a rate of at least 25 cm/sec.

Apparatus 10 may be retrieved to the surface and the data from data logger 16 may then be read out. The data may be processed to yield a visual depiction that allows rapid identification of areas having surface profiles that represent possible problems (e.g. corrosion wear or damage) or other areas of interest (e.g. areas close to tubing joints or other areas where problems are more likely).

Figure 1B:
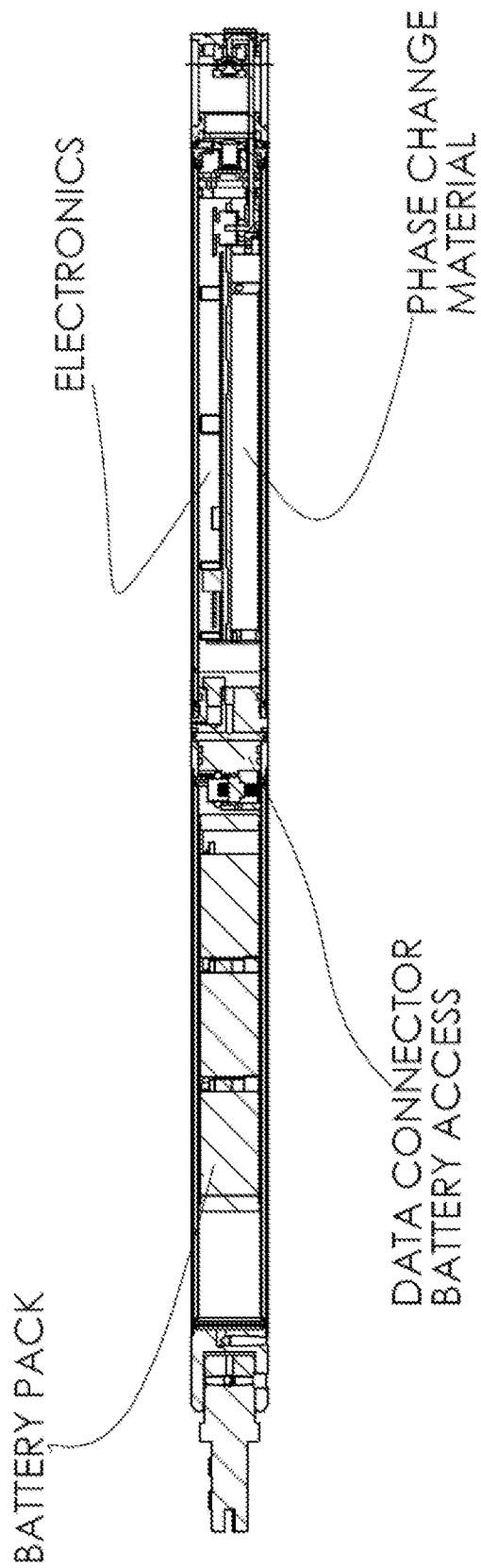

FIG. 1B illustrates apparatus 10A according to a specific example embodiment. Apparatus 10A has a body 12 made up of four parts 12-1, 12-2, 12-3 and 12-4. Parts 12-1 and 12-2 are coupled together at a coupling 13A. Part 12-1 comprises a hollow tube that carries batteries 19 (not shown in FIG. 1A). Fitting 13 is provided on the end of part 12-1.

Coupling 13A includes electrical interfaces to electronics contained within part 12-2, which contains temperature-controlled volume 12C. Part 12-3 is made up of window 12B, and part 12-4 comprises an optical scanning head and is removably coupled at an end of part 12-3.

Figure 2:
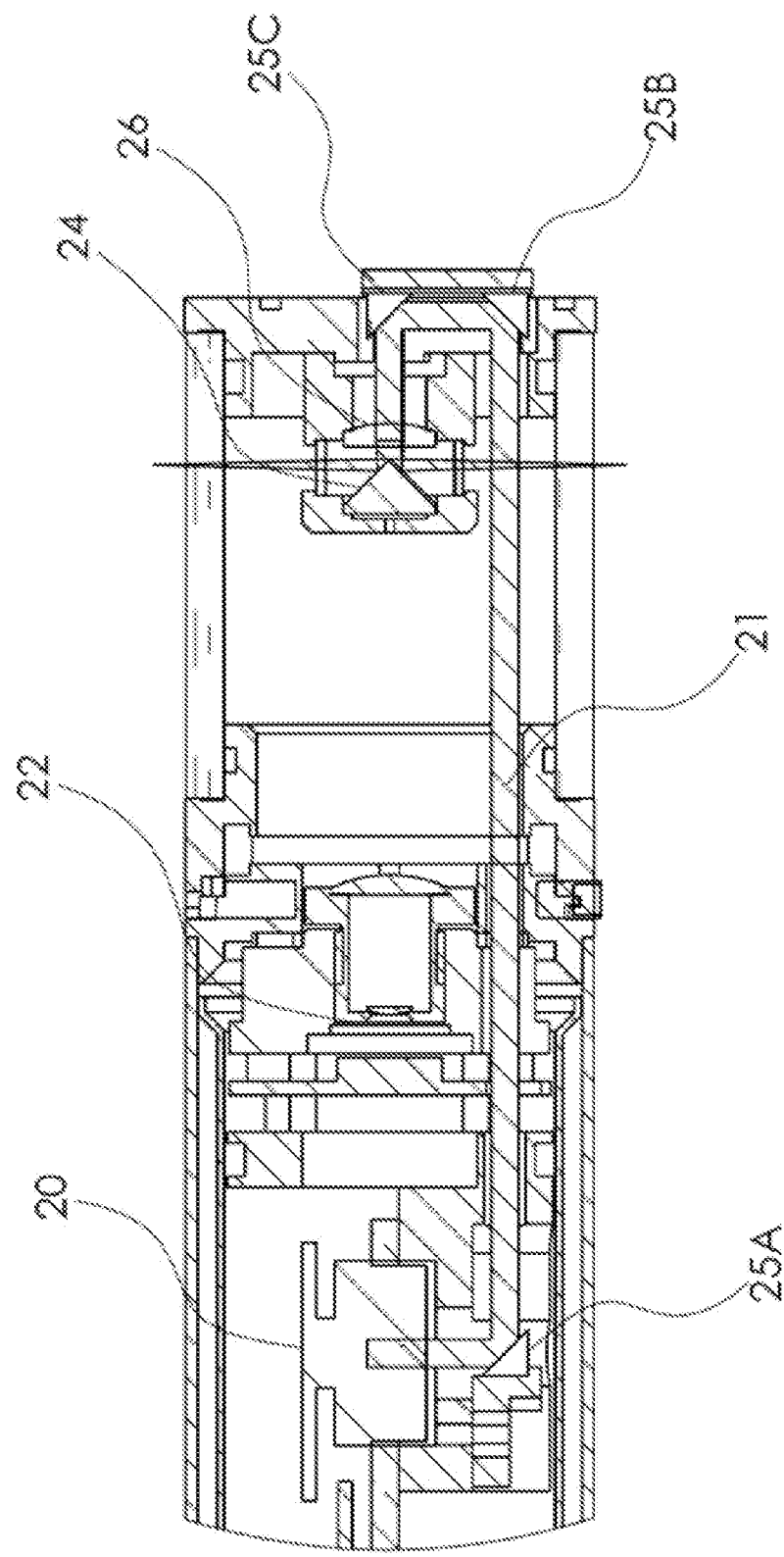
FIGS. 2 and 2A illustrate example optical paths according to different implementations of the invention.

FIG. 2 shows an arrangement of optical components in an example optical scanning system 14. Optical scanning system 14 is similar in operation to the system described in U.S. Pat. No. 8,035,823, however, the components are differently arranged. Optical scanning system 14 includes a laser light source 20 and a camera 22 comprising an imaging sensor array. Light from light source 20 is directed to illuminate the surface of a bore in which apparatus 10 is located. The illuminated surface is imaged by camera 22 and the profiles of the illuminated points relative to apparatus 10 (radial distance as a function of azimuth angle) are determined by triangulation from the images.

A beam 21 of light from laser 20 is directed to impinge in an axial direction on a conical mirror 24. Conical mirror 24 redirects the light from beam 21 into a disc 21A that illuminates a circumferential ring 21B on an inner surface 23 of a bore within which apparatus 10 is located.

Circumferential ring 21B is imaged by camera 22 and the resulting images are processed to determine the profile of surface 23 along the path of ring 21B. The nature of the processing may be as described in U.S. Pat. No. 8,035,823 for example.

In the FIG. 2 implementation, light source 20, which may comprise a solid-state light source such as a laser diode, is oriented to emit beam 21 in a substantially radial direction. Light deflectors 25, such as mirrors or prisms (individually identified as 25A, 25B and 25C), redirect beam 21 to impinge axially on conical mirror 24. In alternative example implementations, light source 20 could be oriented to emit light in a direction parallel to an axis of conical mirror 24. In such alternative implementations, light deflector 25A is not required.

A light deflector 25 redirects beam 21 to proceed generally axially relative to apparatus 10 to light deflectors 25B and 25C which turn beam 21 through 180 degrees to impinge axially on conical mirror 24. Between deflectors 25A and 25B, beam 21 may travel through free space and may pass through disc 21A without interfering with disc 21A.

One or more focus lenses 26 may be provided between light deflector 25C and conical mirror 24 to facilitate efficient distribution of light into disc 21A. Focus lens 26 may be positioned so that light that passes through lens 26 is focused at or near the expected location of a wall of a bore to be inspected after being deflected into disc 21A by conical mirror 24.

Conical mirror 24 is preferably on and aligned with a longitudinal axis of apparatus 10 and window 12B. In the illustrated embodiment, conical mirror 24 faces away from camera 22. This arrangement is advantageous because it places the elements that direct light onto conical mirror 24 (e.g. light deflector 25C) at the end of apparatus 10. This facilitates fine adjustment of such elements to accurately direct light beam 21 onto conical mirror 24 such that light beam 21 is axially aligned with conical mirror 24. This arrangement also places the elements that direct light onto conical mirror 24 out of the view of camera 22.

In the embodiment of FIG. 2, laser light source 20 may emit collimated light. An adjustable lens may optionally be provided to adjust collimation of the light beam emitted by laser light source 20. Lens 26 may then be adjusted so that light projected in disc 21A is focused at the expected location of a bore wall.

The optical arrangement of FIG. 2 is only one example of an optical arrangement operative to carry light from a light source 20 to conical mirror 24 such that the light passes through disc 21A and is then redirected onto conical mirror 24. Another example implementation is illustrated in FIG. 2A.

Figure 2A:
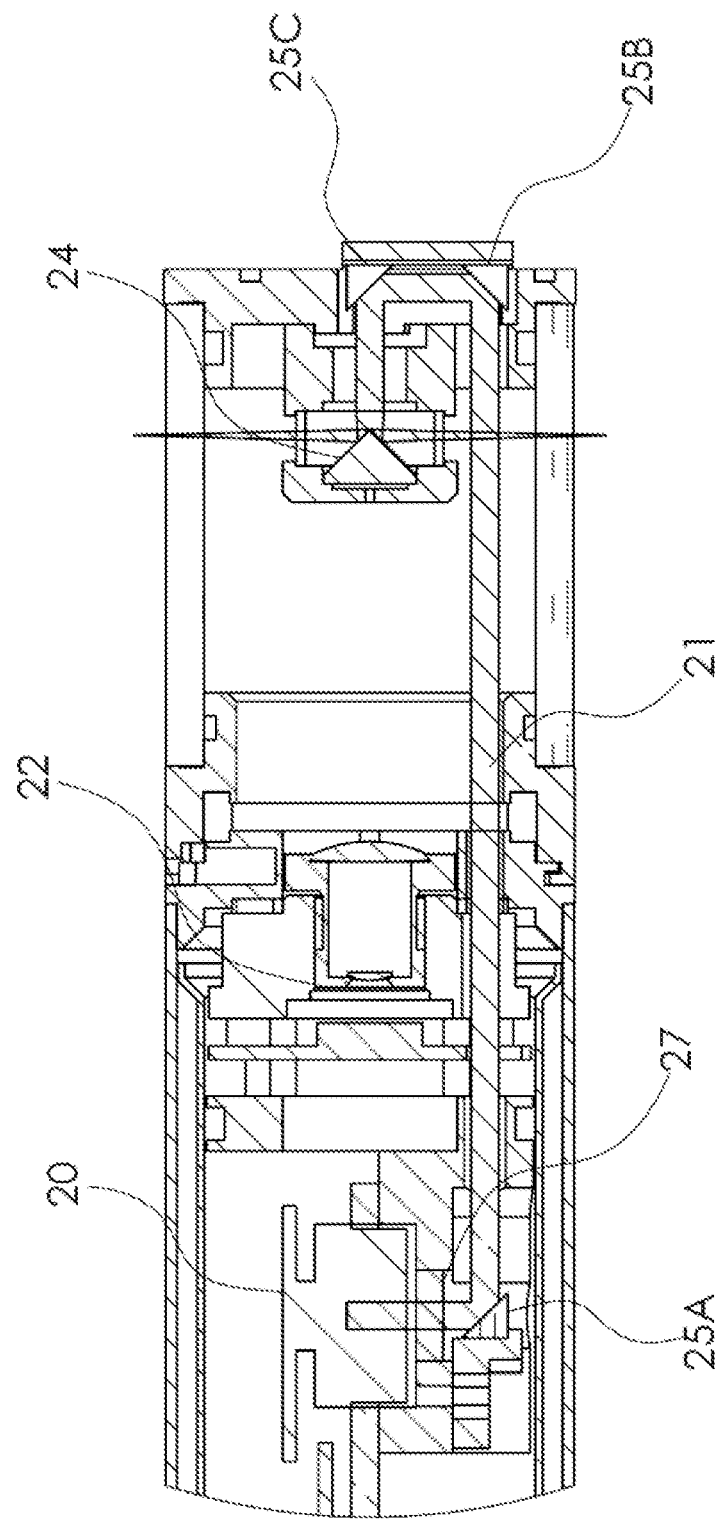

In FIG. 2A an axicon 27 is provided in the optical path upstream from conical mirror 24. An axicon (or "axicon lens") is an optical structure that shapes an input light beam into an output beam that lies on a conical surface having a diameter that increases with distance from the axicon. An axicon may comprise a conical prism. Providing an axicon can be advantageous for reducing the tolerance with which a beam of light from light source 20 must be aligned with conical mirror 24.

In the FIG. 2A implementation, axicon 27 is located immediately after an output lens of laser light source 20. The FIG. 2A implementation lacks a focus lens 26. In the FIG. 2 implementation light from light source 20 may be focused at infinity (collimated beam) and formed by axicon 27 into a beam 21 filling a conical surface of uniform thickness. As in the FIG. 2 implementation, light deflectors 25B and 25C cause beam 21 to turn 180 degrees to impinge on conical mirror 24. In this case, however, the light impinges on conical mirror 24 in a ring.

Light deflectors 25B and 25C may be adjustable to direct light from light source 20 to impinge concentrically on conical mirror 24. In practice, the adjustment can be done to achieve best uniformity of the output light in disc 21A.

It is advantageous to provide conical mirror 24 and the other optical components that are located together with conical mirror 24 as parts of a field-replaceable scanning head 26. Such a scanning head does not require any active electrical components or any wired connection to the rest of apparatus 10 and so may be relatively simple, rugged and/or inexpensive.

In an example embodiment, a part of apparatus 10 which includes scanning head 26 is coupled to the rest of apparatus 10 at a coupling that includes a seal compressed between a pair of flanges. The coupling may be rotatable to facilitate alignment of scanning head 26 with light source 20. In an example implementation, conical mirror 24, light deflectors 25B and 25C and one or more focus lenses 26, if present, are mounted to an end cap that sealingly attaches to close one end of housing 12. The cap may be designed to permit replaceable in the field.

In some implementations, a single pressure seal may be opened to provide access to the interior of housing 12 suitable for most or all routine servicing and operational requirements. For example, in some implementations, housing 12 can be opened at mid length to provide access to one or more batteries, cooling connections and/or data electrical connections.

In the illustrated example embodiment, light source 20 is located behind camera 22 such that camera 22 lies between light source 20 and conical mirror 24. This arrangement has the advantage that light source 20 can be located inside volume 12C where the temperature may be kept to a temperature within an operating temperature range of light source 20. In some embodiments, the upper end of the operating temperature range for light source 20 is at least 60° C. Light source 20 may be mounted to a heat sink that carries away heat from light source 20. The heat sink may be part of temperature control system 18.

In an alternative implementation, light source 20 is mounted to a heat sink that extends from volume 12C to a location closer to conical mirror 24. Such embodiments have the disadvantage that the heat sink and one or more power wires for light source 20 may obstruct scanning in some directions.

Figure 3A:
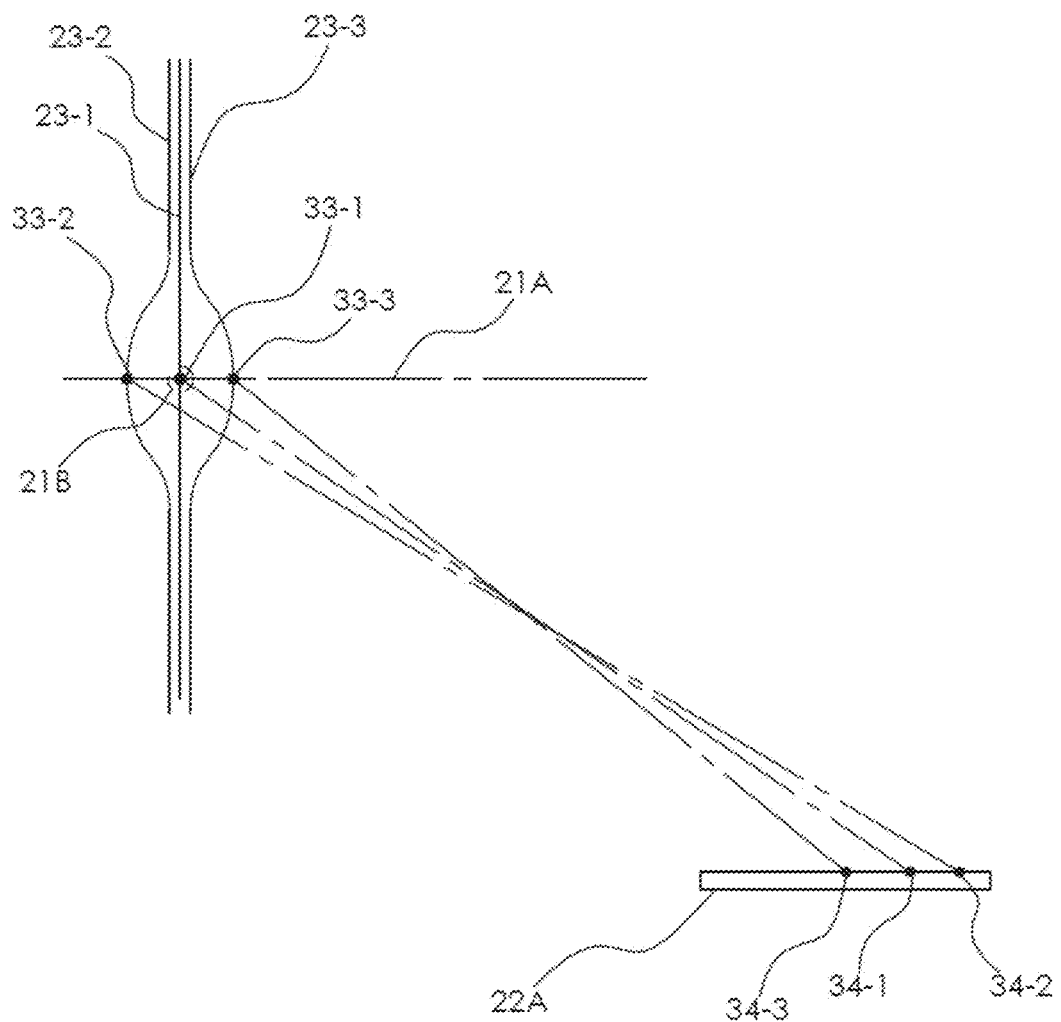
FIGS. 3A and 3B illustrate schematically how a surface profile of points around a circumference of a bore may be determined.
Figure 3B:
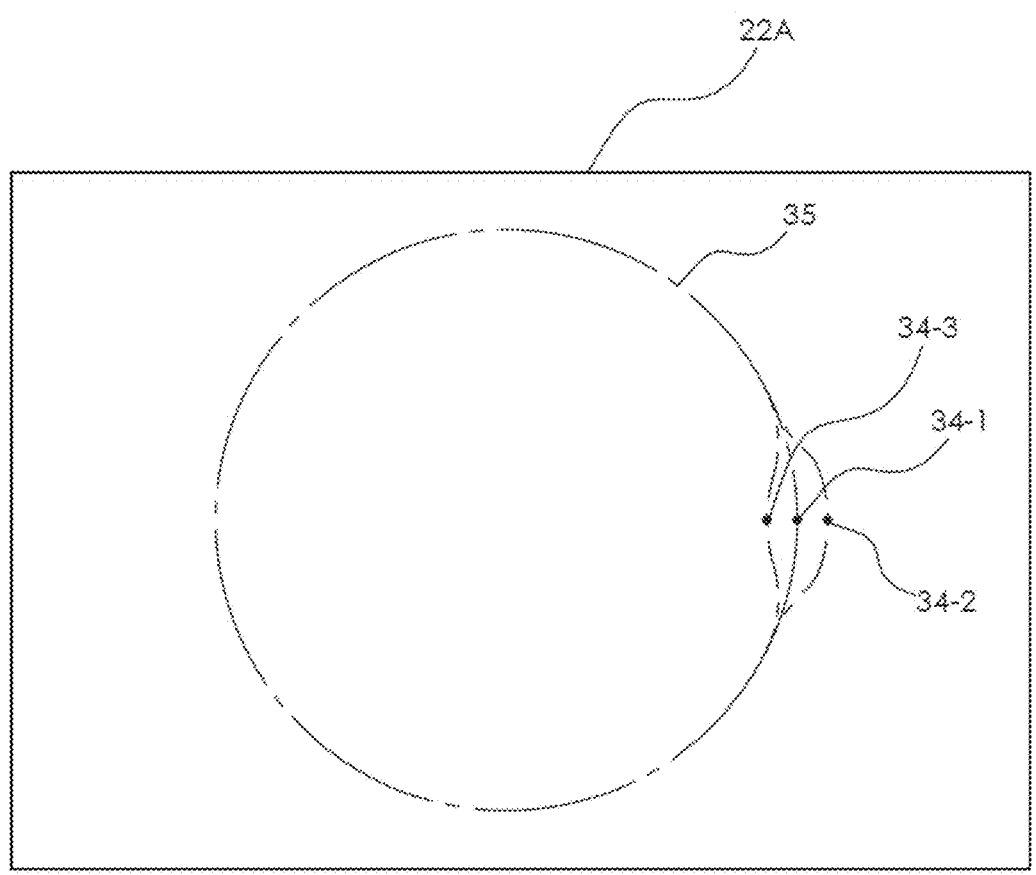

FIGS. 3A and 3B illustrate schematically how a surface profile of points around a circumference of a bore may be determined using apparatus 10. FIG. 3A shows surface 23. Line 35 indicates a cylindrical surface lying at a nominal location of surface 23. Surface 23 may become worn or eroded or corroded at a point so that a particular point on surface 23 is behind surface 31, or surface 23 may become deformed or coated with scale or the like so that a point on surface 23 is in front of surface 31. The elevation of points on surface 23 relative to surface 31 may vary with their position on surface 23.

Light disc 21A illuminates surface 23 at a point 33 along light ring 21B where light disc 21A intersects surface 23. Light ring 21B, including point 33, is imaged onto imaging array 22A of camera 22. Point 33 is imaged onto a corresponding point 34 on imaging array 22A. The radial distance of point 34 from a center of imaging array 22A depends on the profile of surface 23 at the location of point 33.

Camera 22 is calibrated (i.e. points on the imaging array are associated with the coordinates of corresponding points in the plane of light disc 21A). U.S. Pat. No. 8,035,823 describes example ways in which camera 22 may be calibrated.

In the illustrated implementation, camera 22 views the projection of laser disc 21A onto surface 23 in a direction that is perpendicular to laser disc 21A. Processing images from camera 22 yields a collection of points corresponding to surface 23. Using calibration information for camera 22, locations of the points may be expressed in engineering units in an arbitrary coordinate system—usually using the center of the camera field of view as the origin.

Subsequent data processing may be applied to fit/compare profiles of interest to the points. For example, points may be fit to a circle corresponding to the expected ID of tubing that has been scanned. The results of such a fit can indicate where the tube surface deviates from its design location for any reason.

In FIG. 3A, 23-1, 23-2 and 23-3 are three possible profiles for surface 23 in the vicinity of light ring 21 B. Points 33-1, 33-1 and 33-3 respectively lie on example surfaces 23-1, 23-1 and 23-3. Points 34-1, 34-2 and 34-3 are the image points corresponding to points 33-1, 33-2 and 33-3.

Camera 22 preferably has a resolution such that the width of the image 35 of light ring 21B on imaging array 22A is significantly greater than a spacing between adjacent pixels of imaging array 22A. For example, line 35 may have a width of 2 to 3 times a pitch of pixels in array 22A. Electronics of apparatus 10 may be configured to determine the location of a centroid of line 35 in real time at the angular positions of points 34. In some embodiments, the location of the centroid of line 35 is determined with sub-pixel accuracy.

Temperature control system 18 may comprise a container of a material that, upon being heated, experiences an endothermic phase change. The container may comprise a thermally-conductive material, such as copper or another thermally conductive metal. The container may be in thermal contact with light source 20, camera 22 and/or other electronics within volume 12C.

Selecting a phase change material that experiences a phase change within the operating temperature range of light source 20 and other electronics of apparatus 10 can maintain the temperature within volume 12C to be within the operating temperature range for an extended period of time. In an example embodiment, the phase change material has a melting temperature in the range of approximately 45° C. to 65° C. The phase change material may comprise a suitable wax, for example.

Figure 4:
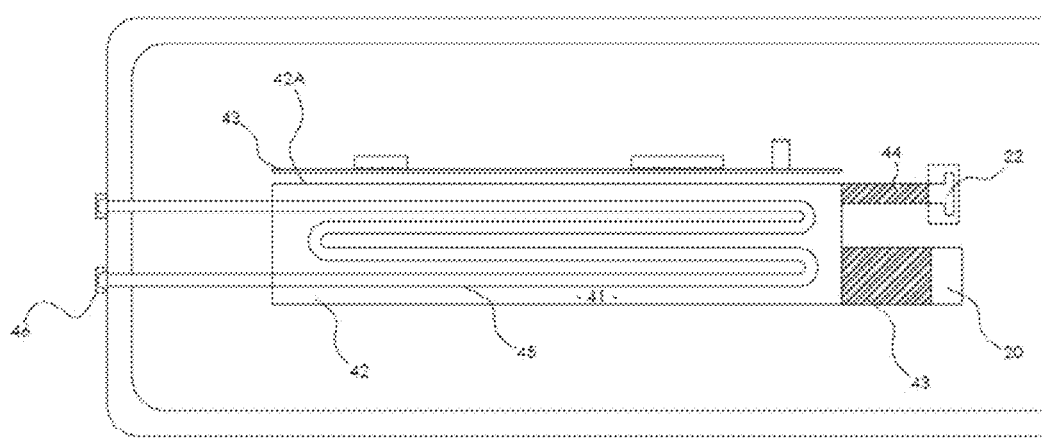
FIG. 4 illustrates apparatus including a temperature control system according to an example embodiment of the invention.

An example temperature control system 18 is illustrated schematically in FIG. 4. In the illustrated example embodiment, a phase change material 41 is enclosed in a container 42. Container 42 may have an elongated format. For example, container 41 may be in the form of a closed-ended tube having one or more flattened sides 42A. For example, the phase change material 41 may be enclosed in a tube that is D-shaped in cross section. One or more circuit boards 43 containing electronics for apparatus 10 (e.g. the circuit boards may carry data logging system 16, controller 17, etc.) may be placed against the flat face 42A of the container 42.

In the illustrated embodiment, container 42 is in close thermal contact with a heat sink 43 of light source 20 and/or a heat sink 44 of camera 22.

In some embodiments, one or more heat-exchange tubes pass 45 are in thermal contact with the phase change material. For example, one or more tubes 45 may be provided in the interior of container 42. After apparatus 10 has been deployed, a cool fluid, such as cold water, may be passed through tubes 45 to withdraw heat from the phase change material and cause a phase change back to a low-temperature phase. In some embodiments, ports 46 provide fluid connections to tubes 45 that are accessible from outside of apparatus 10 so that apparatus 10 may be prepared for re-use without opening apparatus 10.

Batteries 19 may optionally be located outside of volume 12C and/or in a location that is thermally insulated from temperature control system 18. Batteries 19 may be of a type that has an operating temperature range that is broader than the operating temperature range of some of the electronic devices contained in volume 12C. For example, in some embodiments, batteries 19 may operate at temperatures of 85° C. or higher. Batteries 19 may, for example, comprise rechargeable lead-acid type batteries although batteries of other types such as lithium ion may be used in the alternative.

In the illustrated embodiment, window 12B both permits light from optical scanning system 14 to exit from housing 12 to illuminate surface 23 and to enter housing 12 to be detected by camera 22 and also mechanically supports the part of optical scanning system 14 comprising conical mirror 24. Window 12B additionally serves as part of the wall of housing 12 that seals the interior of housing 12 against ingress of dirt or fluids under pressures in the downhole environment. An outer surface of window 12B may be coated to deter adhesion of fluids and/or dirt that may be present in a bore being studied. The coating may comprise a hydrophobic coating and/or an anti-scratch coating and/or an oleophobic coating.

In some implementations, the volume inside window 12B is filled with a transparent material such as an optically clear silicone "jelly". This is particularly practical when optical scanning system 14 has a design that does not require any lenses near conical mirror 24. Filling the chamber behind window 12B with such a material can help to provide a higher pressure rating on window 12B and a more rugged assembly capable of withstanding higher shock loads.

Apparatus 10 may include sensors in addition to optical scanning system 14. For example, apparatus 10 may comprise one or more of: an external pressure sensor, an external temperature sensor, an inertial sensor (e.g. a solid-state gyroscope), a direction sensor (e.g. an inertial sensor and/or a compass), an inclination sensor (e.g. an accelerometer), a magnetometer and a video camera. Outputs of such sensors may be logged by data logger 16. An example implementation comprises a MEMs style sensor providing 3 accelerometer axes oriented for pitch, yaw, and fore/aft acceleration and 3 gyros for "absolute" attitude.

In some embodiments, camera 22 serves both as a camera for optical scanner 14 and as a video or still image camera capable of imaging areas of surface 23. In some embodiments, controller 17 controls camera 22 to acquire video or still images of surface 23 between optical scans. Video or still image data may be stored by data logger 16. In some embodiments, a video or still image is acquired once every N optical scans (where N is a suitable integer). N may optionally be selected such that images of the entire surface 23 are obtained.

In an example embodiment, apparatus 10 comprises an additional light source (e.g. an LED light source) which is used for video or still imaging. To obtain a video or still image, light source 20 may be turned off and the additional light source may be turned on.

Figure 5:
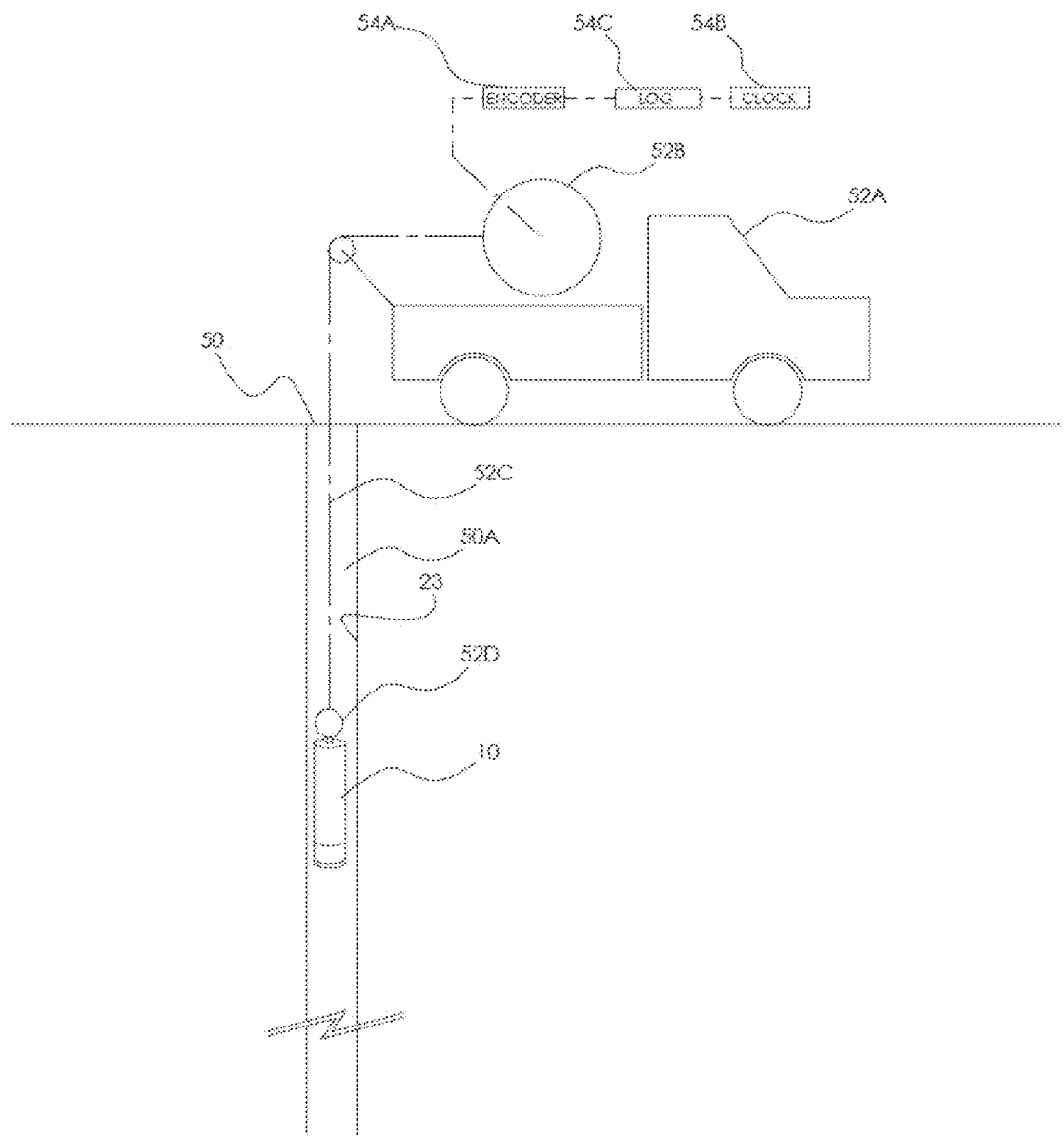
FIG. 5 illustrates an example application in which apparatus as described according to an example embodiment is deployed by a slickline truck in a wellbore.

FIG. 5 illustrates an example application. An objective is to obtain information regarding the surface 23 within the bore 50A of a well 50. Surface 23 may comprise an as-drilled wellbore, the inner surface of a casing installed in well 50 or the inner surface of production tubing deployed in well 50, for example. The information may be required after drilling well 50 to assess the need for casing and cement at locations in the wellbore or at a later time to detect damage and/or corrosion within the wellbore.

A truck 52A carrying a winch 52B lowers a slickline 52C into well 50. A weight 52D is attached near a lower end of slickline 52C. Apparatus 10 is attached to slickline 52C below weight 52D. Prior to deploying apparatus 10 slickline 52C may be operated to lower a cleaner such as a wire brush down well 50 so as to remove contaminants such as waxes, oils, dirt or the like from surface 23.

Advantageously, apparatus 10 can operate autonomously and does not require data or power connections to the surface in order to operate. Apparatus 10 acquires surface profile information, as described herein, either or both while apparatus 10 is being lowered into well 50 by winch 52B and while apparatus is being retrieved from well 50 by winch 52B. The profile information may comprise a complete 360 degree profile measured at a desired longitudinal (axial) resolution over all or a desired portion of the bore of well 50. Once apparatus 10 is back at the surface the surface profile information may be downloaded from apparatus 10 and processed/reviewed to identify features such as areas in which surface 23 may be damaged, corroded, worn or the like and/or to confirm that surface 23 maintains a desired level of integrity.

Apparatus 10 may be configured to automatically initiate a survey and/or terminate a survey based, for example, on readings of sensors provided in apparatus 10. For example, a survey may be initiated in response to detecting that apparatus 10 has a first attitude, is exposed to a first pressure and/or light level, is detecting or not detecting a signal and/or that a clock of apparatus 10 is indicating a first time. Similarly, a survey may be terminated by apparatus 10 in response to detecting that apparatus 10 has a second attitude, is exposed to a second pressure and/or light level, is detecting or not detecting a signal and/or that a clock of apparatus 10 is indicating a first time.

The equipment used to deploy apparatus 10 may be a winch truck of the type that is readily available and standard in well-servicing operations. The illustrated embodiment includes an optional system including an encoder 54A that measures the travel of slickline 52C, a real-time clock 54B and a data logging device 54C that records positions of slickline 52C as measured by encoder 54A at various times as measured by clock 54B. Data from data logging system 54C may be combined with data connected by apparatus 10 to provide more accurate depth information for points measured by apparatus 10.

The data obtained by apparatus 10 may then be processed to obtain information of interest. Since apparatus 10 can provide digital values that indicate directly the profile of the interior of well 50 (or some other structure being studied), it is relatively straightforward to process the data to reveal areas in which the surface profile exceeds set limits. Other measures that may be readily computed include minimum and maximum radial distances of wall 23 from a centerline of the bore being studied (these measures relate directly to wall thickness values if the outer diameter of the tubular is known) and the like.

In some implementations, a point cloud obtained by apparatus 10 is processed to obtain location information that identifies locations that may correspond to corrosion or damage. The location information may be used, for example, to obtain more information about the condition of the bore at the locations. For example, the location information may be used to:

select parts of separately acquired image data or video data corresponding to the locations so that the image or video data can be reviewed by a person; or guide apparatus 10 or another apparatus to acquire images or video data corresponding to the locations; or select from a set of sensor data, sensor data corresponding to the locations; or guide apparatus 10 or other apparatus to acquire sensor data at the locations.

In an example application, apparatus 10 is deployed in a bore and operates to acquire a point cloud that characterizes a surface of the bore. Apparatus 10 is retrieved and the point cloud is processed to obtain location information. Apparatus 10 or another apparatus is then operated to obtain more information (e.g. still images, video images and/or sensor data) about the locations specified in the location information.

In another example implementation, the point cloud is processed to obtain the location information by a processor of apparatus 10. In such implementations, apparatus 10 may operate autonomously to obtain more information (e.g. still images, video images and/or sensor data) about the locations specified in the location information. For example, the point cloud may be obtained while apparatus 10 is being moved in one direction along a bore (e.g. while apparatus 10 is being lowered into a bore), and additional information about the locations may be obtained automatically by apparatus 10 while apparatus 10 is moving in the other direction along the bore (e.g. while apparatus 10 is being recovered from the bore). As another example, apparatus 10 may process the point clouds as they are obtained and may obtain and/or flag video, still images and/or other sensor information corresponding to locations for which analysis of the point cloud indicates the possibility of corrosion or other damage.

Some implementations process a point cloud obtained by apparatus 10 in a bore to generate 3D representations of the bore. Areas that may be subject to corrosion or other damage may be automatically highlighted.

For example, information regarding the profile of the bore of production tubing obtained by apparatus 10 may be processed to identify areas of sucker rod damage. There may be no such areas or only a few such areas in long stretches of the production tubing which may have a length of several thousand feet or meters. An advantage of some embodiments is that this analysis may be automated. Only those areas of possible interest due to corrosion or build up are identified for a human observer to examine. In contrast, video inspection data must generally be viewed in its entirety by a human.

Since wear due to sucker rods will most likely be at the inside of any curves in the well trajectory, some implementations take into account curvature of the well trajectory (e.g. as determined by changes in the attitude of apparatus 10 as measured by an onboard accelerometer or other inclination sensor) in identifying areas of potential damage (e.g. sucker rod damage).

Figure 6:
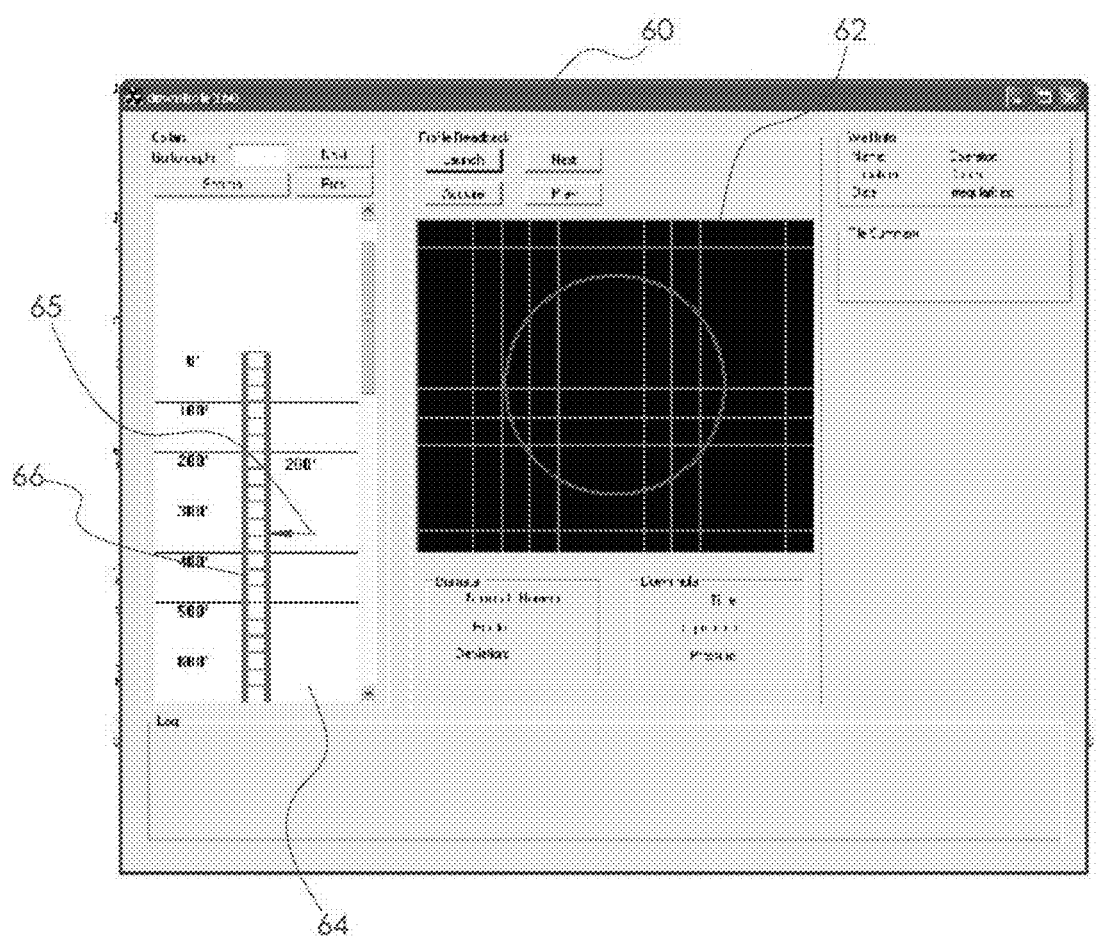
FIG. 6 depicts a display produced by an example software application which processes data retrieved by apparatus as described herein.

FIG. 6 illustrates an example display 60 that may be produced by software analyzing the data acquired by apparatus 10. Display 60 includes an area 62 that graphically depicts a profile 62A measured at a selected location along a bore being studied. Display 60 also includes an area 64 that schematically illustrates the section(s) of a bore for which data has been received. A pointer 65 or other indicia in area 64 may indicate the longitudinal position at which the profile currently on display in area 62 was acquired.

In the illustrated embodiment, area 64 graphically illustrates positions of tool joints 66 detected by apparatus 10. Tool joints 66 are the locations at which tubular elements which make up casing or production tubing are coupled to one another.

Display 60 may also include indicia indicating any location(s) at which anomalies have been detected. Examples anomalies that the software may scan for include:

points on surface 23 that exceed a threshold radial distance from a fitted reference surface (e.g. a circle or rectangle);

areas of surface 23 wherein the surface profile exhibits more than a threshold amount of variation (indicating irregular surfaces).

Apparatus as described herein may provide an autonomous platform capable of deploying sensors inexpensively and effectively in high pressure and temperature environments. Although it is advantageous to provide a tool that can be deployed without any power or data connections, one could optionally provide a version of apparatus 10 that uses power or data connections to an external device (e.g. a surface station). Such apparatus could be used, for example, with an e-line which provides plural conductors for communication with apparatus 10. In such embodiments, data logger 16 and/or batteries 19 may not be required or provided.

Some disclosed embodiments have the advantage that there are no wires, supports, structural member or other elements that obstruct the view of the portion of bore wall illuminated by light disc 21A by a camera 22.

Apparatus 10 has been described as including various electronic systems such as data logger 16, controller 17 and camera 22. There is a wide variety of ways to implement such systems as is known to those of skill in the art. Example embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")).

Examples of programmable data processors are: microprocessors, digital signal processors ("DSPs"), embedded processors, graphics processors, math co-processors, general purpose computers, and the like. For example, one or more data processors in a control circuit of apparatus 10 may implement methods as described herein by executing software instructions in a program memory accessible to the one or more processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. In other alternative cases processes or blocks are performed simultaneously or in different sequences. Each of these processes or blocks may be implemented in a variety of different ways. Also, while processes or blocks are at times shown as being performed in series, these processes or blocks may instead be performed in parallel, or may be performed at different times.

Certain aspects of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted. In non-limiting example embodiments the program product contains one or more of: instructions for controlling apparatus 10 to acquire data; and instructions for processing data acquired by an apparatus 10.

Interpretation of Terms

Unless the context clearly requires otherwise, throughout the description and the claims:
 "comprise", "comprising", and the like are to be construed in an inclusive sense, as opposed to an exclusive or exhaustive sense; that is to say, in the sense of "including, but not limited to";
 "connected", "coupled", or any variant thereof, means any connection or coupling, either direct or indirect, between two or more elements; the coupling or connection between the elements can be physical, logical, or a combination thereof;
 "herein", "above", "below", and words of similar import, when used to describe this specification, shall refer to this specification as a whole, and not to any particular portions of this specification;
 "or", in reference to a list of two or more items, covers all of the following interpretations of the word: any of the items in the list, all of the items in the list, and any combination of the items in the list;
 the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. Apparatus useful for profiling a wall of a bore, the apparatus comprising:
 an optical scanning system comprising: a light source, optical elements arranged to direct light from the light source to be incident in an axial direction onto a reflective surface of a conical mirror and a camera, the reflective surface of the conical mirror facing away from the camera;
 wherein the conical mirror is operative to redirect the incident light into a disc of light, the light source and the camera are both on one side of the disc of light, the camera is located to view an intersection of the disc of light with the wall of the bore and the optical elements include one or more elements arranged to receive the light and reverse a direction of propagation of the light upstream from the conical mirror.

2. Apparatus according to claim 1 comprising a housing enclosing the optical scanning system, the housing comprising a generally cylindrical body, at least a portion of a wall of the housing comprising a cylindrical window located to allow light in the disc of light to pass through the window and to allow the camera to view the intersection of the disc of light with the wall of the bore through the window.

3. Apparatus according to claim 2 wherein the optical elements comprise first and second light deflecting elements located between the conical mirror and a first end of the housing on an opposite side of the conical mirror from the camera, each of the optical elements arranged to deflect the light through a right angle.

4. Apparatus according to claim 3 wherein the light source is arranged to emit light in a radial direction and the optical elements comprise a third light deflector arranged to redirect the light to propagate to the first light deflecting element in a direction parallel to the axial direction.

5. Apparatus according to claim 3 wherein the optical elements comprise an axicon located between the light source and the first light deflector.

6. Apparatus according to claim 2 wherein the camera lies between the light source and the conical mirror.

7. Apparatus according to claim 2 wherein for at least a portion of the length of the window, the interior of the housing is empty.

8. Apparatus according to claim 2 comprising a temperature control system within the housing, the temperature control system comprising a volume of material that, upon being heated, experiences an endothermic phase change.

9. Apparatus according to claim 8 wherein the material is enclosed in a thermally-conductive container and the camera is mounted to a heat sink in thermal contact with the thermally-conductive container.

10. Apparatus according to claim 8 wherein the material is enclosed in a thermally-conductive container and the light source is mounted to a heat sink in thermal contact with the thermally-conductive container.

11. Apparatus according to claim 8 wherein the volume of material is located in a thermally-protected portion of the housing wherein the walls of the housing are thermally-insulated.

12. Apparatus according to claim 11 wherein the thermally-protected portion of the housing is double-walled.

13. Apparatus according to claim 2 wherein the camera and light source are powered by one or more batteries located within the housing and the apparatus comprises a data-logger within the housing, the data logger connected to record data acquired by the camera.

14. Apparatus according to claim 2 comprising a fitting operable to couple the housing to a slickline.

15. Apparatus according to claim 2 wherein the housing is cylindrical and has a diameter less than 1.9 inches.

16. Apparatus according to claim 2 comprising one or more centralizing features projecting radially from the housing.

17. Apparatus according to claim 16 wherein the centralizing features comprise resilient bows or arms or wipers.

18. Apparatus according to claim 2 comprising a controller configured to operate the camera to periodically measure the profile of a set of points on a circumference of the bore wall at one longitudinal position along the bore wall.

19. Apparatus according to claim 18 comprising a real-time clock and a data logger configured to store the measured profiles and corresponding times from the real-time clock at which the measured profiles were measured.

20. Apparatus according to claim 1 wherein the optical scanning system is operative to acquire data indicative of a surface profile of the bore at an intersection of the disc of light with the wall of the bore with an angular separation between adjacent points of 1 degree or less.

21. Apparatus according to claim 1 wherein the optical scanning system 14 is configured to provide a complete 360 degree profile of a bore wall relative to a reference origin of the optical scanning system.

* * * * *

UNITED STATES PATENT AND TRADEMARK OFFICE
CERTIFICATE OF CORRECTION

PATENT NO. : 10,267,725 B2
APPLICATION NO. : 15/987025
DATED : April 23, 2019
INVENTOR(S) : John Howard Keightley and Adriano Goncalves Cunha It is certified that error appears in the above-identified patent and that said Letters Patent is hereby corrected as shown below:

On the Title Page

Item (73), the name and address of the Assignee is corrected from "Evolution Engineering Inc., Calgary (CA)" to --3DM Devices Inc., Aldergrove (CA)--.

Signed and Sealed this
Third Day of March, 2020

Andrei Iancu
*Director of the United States Patent and Trademark Office*